US00PP08173P

United States Patent [19]

Schumann

[11] Patent Number: Plant 8,173

[45] Date of Patent: Mar. 9, 1993

[54] GERANIUM PLANT NAMED FISLANTIS

[75] Inventor: Ingeborg Schumann, Münster, Fed. Rep. of Germany

[73] Assignee: Florfis AG, Binningen, Switzerland

[21] Appl. No.: 779,542

[22] Filed: Oct. 18, 1991

[51] Int. Cl.[5] ..... A01H 5/00
[52] U.S. Cl. ..... Plt./87.12
[58] Field of Search ..... Plt./87.12

*Primary Examiner*—James R. Feyrer
*Attorney, Agent, or Firm*—Foley & Lardner

[57] ABSTRACT

A new and distinct cultivar of Geranium named Fislantis, particularly characterized by its rose or cherry red flower color, semi-double flower form, dark green foliage without zonation, compact growth habit, and early flower response.

1 Drawing Sheet

The present invention comprises a new and distinct cultivar of Geranium, botanically known as *Pelargonium zonale,* and hereinafter referred to by the cultivar name Fislantis.

Fislantis is a product of planned breeding program which had the objective of creating new geranium cultivars with cherry red flower color, semi-double flower form, dark foliage and compact habit.

Fislantis was originated from a hybridization made by the inventor Ingeborg Schumann in a controlled breeding program in Galdar, Gran Canaria, Spain in 1985. The female parent was Flirtpel (U.S. Plant Pat. No. 5,369), characterized by its bluish-pink flower color and short plant habit. The male parent of Fislantis was an inbred seedling of a hybrid resulting from a cross between the cultivar Drepenosa (also known by trademark "Dresdner Puppe") and a tetraploid line of Stadt Bern. The cultivar Stadt Bern is characterized by single red flowers and very dark foliage.

Fislantis was discovered and selected as one flowering plant within the progeny of the stated cross by Ingeborg Schumann in 1986 in a controlled environment in Galdar, Gran Canaria, Spain.

The first act of asexual reproduction of Fislantis was accomplished when vegetative cuttings were taken from the initial selection in 1987 in a controlled environment in Hillscheid, Federal Republic of Germany by, or under the supervision of, Ingeborg Schumann.

Horticultural examination of selected units initiated in May 1987 and continuing thereafter has demonstrated that the combination of characteristics as herein disclosed for Fislantis are firmly fixed and are retained through successive generations of asexual reproduction.

Fislantis has not been observed under all possible environmental conditions. The phenotype may vary somewhat with variations in environment such as temperature, light intensity and day length, without, however, any variance in the genotype. The following observations measurements, and comparisons describe plants grown in Hillscheid, Federal Republic of Germany under greenhouse conditions which approximate those generally used in commercial practice.

The following traits have been repeatedly observed and are determined to be basic characteristics of Fislantis, which in combination distinguish this Geranium as a new and distinct cultivar:

1. Rose red flower color
2. Semi-double flower form
3. Large umbels

4. Dark foliage without zonation
5. Comparative early flower response for a dark foliaged cultivar
6. Compact plant habit
7. Good branching characteristics Of the many commercial cultivars known to the present inventor, the most similar in comparison to Fislantis is Disco, disclosed in U.S. Plant Pat. No. 5,930. Reference is made to attached Chart A which compares certain characteristics of Fislantis to those same characteristics of Disco. In general comparison to Disco, Fislantis has darker green foliage, smaller leaves, more compact growth habit, flowers without markings (eyes) on petals, and a rose red flower color as opposed to the more vivid, intense red of Disco.

The accompanying color photographic drawing is a top perspective view showing typical flower and foliage characteristics of Fislantis, with colors being as true as possible with illustrations of this type.

In the following description color references are made to the Royal Horticultural Society Colour Chart. The color values were determined indoors from flowers taken from plants grown outdoors in June at Hillscheid, Federal Republic of Germany.

Classification:

*Botanical.*—A hybrid of the species *Pelargonium zonale L'Hert.*

*Commercial.*—Zonal Geranium, cv. Fislantis.

INFLORESCENCE

A. Umbel:

*Average diameter.*—112 mm.
*Average depth.*—60 mm.
*Peduncle length.*—160 mm.
*Pedicel length.*—30 mm.
*Pedicel color.*—Red (anthocyanin colored).
*Number of flowers per umbel.*—About 40–50.

B. Corolla:

*Average diameter.*—49 mm.
*Form.*—Semi-double.
*Number of petals.*—12–14.
*Color (general tonality from a distance of three meters).*—Red.
*Color of upper petals.*—Between 52A and 57C.
*Color of lower petals.*—Approximately 57C tips.

C. Bud:

*Shape.*—Round, pointed.

*Color (sepals).*—Green, with anthocyanin at the base.

*Color (tips of petals).*—Rose red.

D. Reproductive organs:

*Androecium.*—5–7 fertile anthers, with orange pollen.

*Gynoecium.*—5–6 lobed stigma, red.

E. Spring flowering response period: In Hillscheid, Federal Republic of Germany, in 1989 85% of plants with at least 1 flower opened 13 weeks after planting of unrooted cuttings.

F. Outdoor flower production: The flower count in 1989 in Hillscheid, Federal Republic of Germany indicated between 50 and 55 flowers per plant for May through September observation period.

G. Durability: Medium rain resistance.

PLANT

A. Foliage:

*Form.*—Kidney-shaped to round, base of leaf not quite closed.

*Margin.*—Bicrenate.

*Color (upper surface).*—Dark green, approximately R.H.S. 137 A-B.

*Color (zonation).*—Very slight zonation.

*Tolerance of botrytis.*—Medium.

B. General appearance and form:

*Internode length.*—1–2 cm.

*Branching pattern.*—3.5 branches after 14 weeks of growing time.

*Height.*—Comparatively low: 23 cm in August.

CHART A

| | FISLANTIS | DISCO |
|---|---|---|
| Flower Color | Between 52A and 57C | 45B with purple tinging |
| Markings of flower petals | No markings | Purple eye |
| Color of peduncles | Red | Green |
| Color of pedicels | Entirely red | Green and red |
| Color of leaf | Dark green | Medium green |
| Growth | Weak | Weak to medium |
| Plant habit | Compact | Compact to medium |
| Height of foliage | 23 cm | 26 cm |

I claim:

1. A new and distinct cultivar of Geranium plant named Fislantis, as illustrated and described.

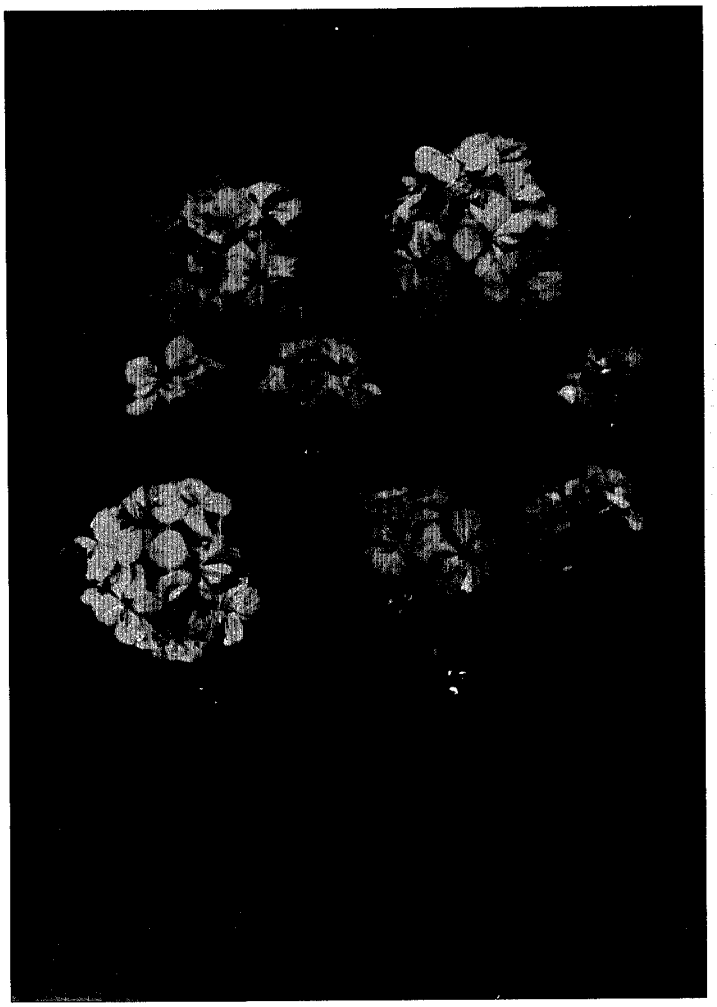

* * * * *